(12) United States Patent
Maskara et al.

(10) Patent No.: US 8,463,377 B2
(45) Date of Patent: Jun. 11, 2013

(54) TEMPERATURE ASSISTED STIMULATION

(75) Inventors: Barun Maskara, Blaine, MN (US);
Jason J. Hamann, Blaine, MN (US);
Stephen Ruble, Lino Lakes, MN (US);
Craig Stolen, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 407 days.

(21) Appl. No.: 12/775,215

(22) Filed: May 6, 2010

(65) Prior Publication Data
US 2010/0305632 A1 Dec. 2, 2010

Related U.S. Application Data

(60) Provisional application No. 61/181,041, filed on May 26, 2009.

(51) Int. Cl.
*A61N 1/18* (2006.01)
*A61N 1/00* (2006.01)
*A61F 7/00* (2006.01)
*A61F 7/12* (2006.01)

(52) U.S. Cl.
USPC ...... 607/3; 607/2; 607/99; 607/116; 607/118; 607/119

(58) Field of Classification Search
USPC .......................................................... 607/3
See application file for complete search history.

(56) References Cited

U.S. PATENT DOCUMENTS

| | | | | |
|---|---|---|---|---|
| 5,314,423 | A * | 5/1994 | Seney | 606/20 |
| 6,258,084 | B1 * | 7/2001 | Goldman et al. | 606/32 |
| 6,415,183 | B1 | 7/2002 | Scheiner et al. | |
| 6,772,008 | B2 | 8/2004 | Zhu et al. | |
| 7,203,537 | B2 * | 4/2007 | Mower | 607/3 |
| 7,299,093 | B2 | 11/2007 | Zhu et al. | |
| 7,392,086 | B2 | 6/2008 | Sathaye | |
| 2002/0087146 | A1 * | 7/2002 | Schu et al. | 604/891.1 |
| 2003/0171685 | A1 * | 9/2003 | Lesser et al. | 600/509 |
| 2003/0181949 | A1 * | 9/2003 | Whale | 607/2 |
| 2003/0225331 | A1 * | 12/2003 | Diederich et al. | 600/437 |
| 2004/0082984 | A1 * | 4/2004 | Osorio et al. | 607/105 |

(Continued)

OTHER PUBLICATIONS

Kiernan, Matthew C., et al., "Effects of temperature on the excitability properties of human motor axons", *Brain*, 124, (2001), 816-825.

(Continued)

*Primary Examiner* — Carl H Layno
*Assistant Examiner* — Erin Piateski
(74) *Attorney, Agent, or Firm* — Schwegman Lundberg & Woessner, P.A.

(57) ABSTRACT

Various embodiments of an implantable system for delivering therapy comprise at least one of a heat sink or source to either reduce or increase temperature of excitable tissue, a pulse generator and at least one stimulation electrode to deliver electrical stimulation to excitable tissue, a memory and a controller. The memory has instructions for performing at least one stimulation routine and at least one thermal routine, and further has integration instructions for integrating the thermal routine(s) with the stimulation routine(s). The controller is configured to operate on the instructions to perform the stimulation routine(s) using the pulse generator and the at least one stimulation electrode, to perform the thermal routine(s) using the heat sink or the heat source, and to operate on the integration instructions to integrate thermal routine(s) with the stimulation routine(s).

24 Claims, 10 Drawing Sheets

U.S. PATENT DOCUMENTS

| | | | |
|---|---|---|---|
| 2005/0149123 A1* | 7/2005 | Lesser et al. | 607/2 |
| 2007/0150006 A1* | 6/2007 | Libbus et al. | 607/2 |
| 2008/0015667 A1* | 1/2008 | Gross | 607/113 |
| 2008/0058892 A1* | 3/2008 | Haefner et al. | 607/45 |
| 2008/0086181 A1* | 4/2008 | Amurthur et al. | 607/45 |
| 2008/0161894 A1* | 7/2008 | Ben-David et al. | 607/116 |
| 2008/0243212 A1 | 10/2008 | Lovett et al. | |
| 2008/0319513 A1* | 12/2008 | Pu et al. | 607/62 |

OTHER PUBLICATIONS

Klumpp, D., et al., "Irreversible Differential Block of A- and C-Fibres Following Local Nerve Heating in the Cat", *J. Physiol.*, 298, (1980), 472-482.

* cited by examiner

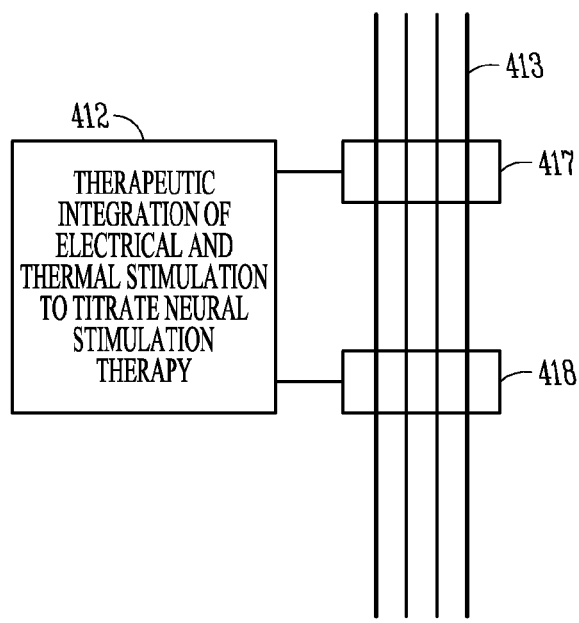
*FIG. 4A*
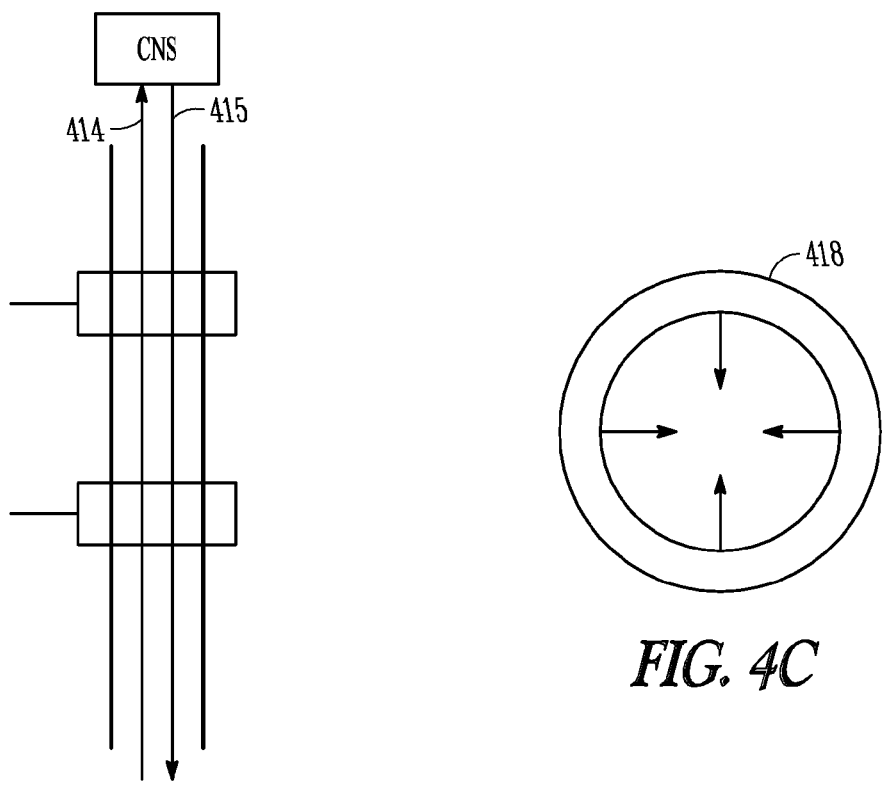
*FIG. 4B*
*FIG. 4C*

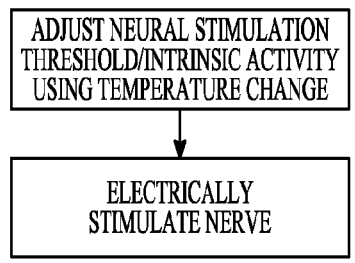
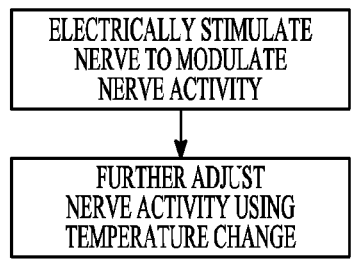
FIG. 5  FIG. 6
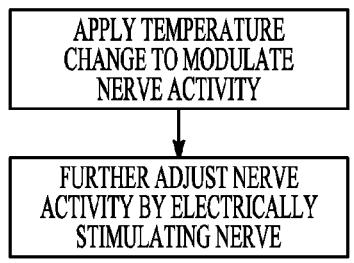
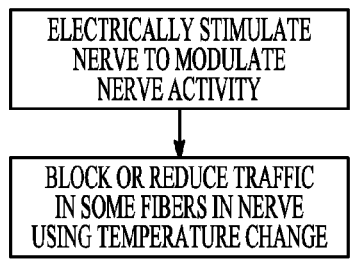
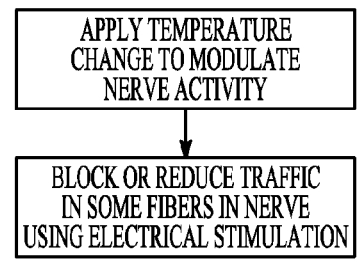
FIG. 7  FIG. 8  FIG. 9
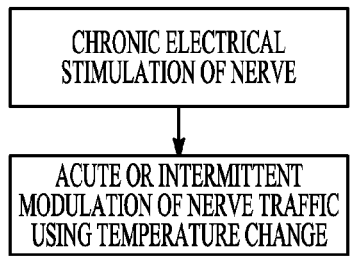
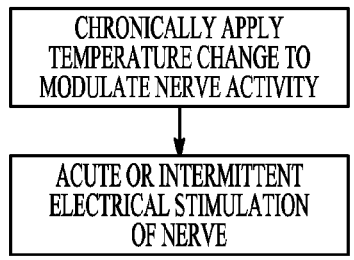
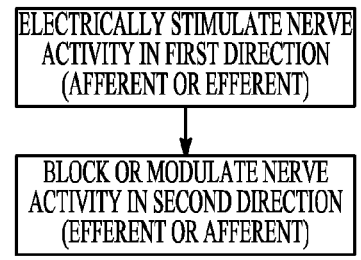
FIG. 10  FIG. 11  FIG. 12

TEMPERATURE ASSISTED STIMULATION

CROSS-REFERENCE TO RELATED APPLICATION

This application claims the benefit of U.S. Provisional Application No. 61/181,041, filed on May 26, 2009, under 35 U.S.C. §119(e), which is hereby incorporated by reference in its entirety.

TECHNICAL FIELD

This application relates generally to medical devices and, more particularly, to systems, devices and methods for temperature-assisted stimulation of tissue such as neural tissue and cardiac tissue.

BACKGROUND

Implantable cardiac devices provide electrical stimulation to selected chambers of the heart to treat a number of cardiac disorders. A pacemaker, for example, is a device which paces the heart with timed pacing pulses. A pacemaker may treat bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed to promote efficient pumping of blood by affecting the manner and degree to which the heart chambers contract. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction.

In addition to cardiac tissue, another type of excitable tissue that propagates action potentials is neural tissue. Centrally mediated reflex pathways modulate cardiac rate, contractility, and excitability. Baroreceptors and chemoreceptors in the heart, great vessels, and lungs transmit cardiac activity through vagal and sympathetic afferent fibers to the central nervous system. Some neural stimulators treat a variety of disorders, such as epilepsy, obesity, and breathing disorders. Neural stimulation has also been proposed for various cardiovascular disorders. Experimentally, neural stimulation has been shown to have a significant effect on several cardiovascular conditions, and may be used to treat hypertension, remodeling after myocardial infarction, and heart failure. Modulation of the sympathetic and parasympathetic nervous system with neural stimulation has been shown to have positive pre-clinical and clinical benefits, such as protecting the myocardium from further remodeling and from a predisposition to fatal arrhythmias following a myocardial infarction.

SUMMARY

Various embodiments of an implantable system for delivering therapy comprise at least one of a heat sink or source to either reduce or increase temperature of excitable tissue, a pulse generator and at least one stimulation electrode to deliver electrical stimulation to excitable tissue, a memory and a controller. The memory has instructions for performing at least one stimulation routine and for performing at least one thermal routine, and further has integration instructions for integrating the at least one thermal routine with the at least one stimulation routine. The controller is configured to operate on the instructions to perform the at least one stimulation routine using the pulse generator and the at least one stimulation electrode, to perform the at least one thermal routine using the heat sink or the heat source, and to operate on the integration instructions to integrate the at least one thermal routine with the at least one stimulation routine.

According to various embodiments of a method for stimulating cardiac tissue, a stimulation threshold of excitable tissue is changed from a first level to a second level in preparation for stimulating the cardiac tissue, where changing the stimulation threshold of the excitable tissue includes changing a temperature of the excitable tissue. The cardiac tissue is stimulated when the stimulation threshold is at the second level.

According to various embodiments of a method for stimulating nerve tissue, a stimulation threshold of excitable tissue is changed from a first level to a second level in preparation for stimulating the nerve tissue, where changing the stimulation threshold of the excitable tissue includes changing a temperature of the excitable tissue. The nerve tissue at a stimulation site is stimulated when the stimulation threshold is at the second level.

According to various embodiments of a method for stimulating nerve tissue, a first neural target is electrically stimulated, and a temperature of a second neural target is changed.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 4A-4C illustrate a device embodiment.

FIGS. 5-12 illustrate various methods, by way of example and not limitation, that can be performed using the device illustrated in FIG. 4A.

DETAILED DESCRIPTION

Figure 1A:
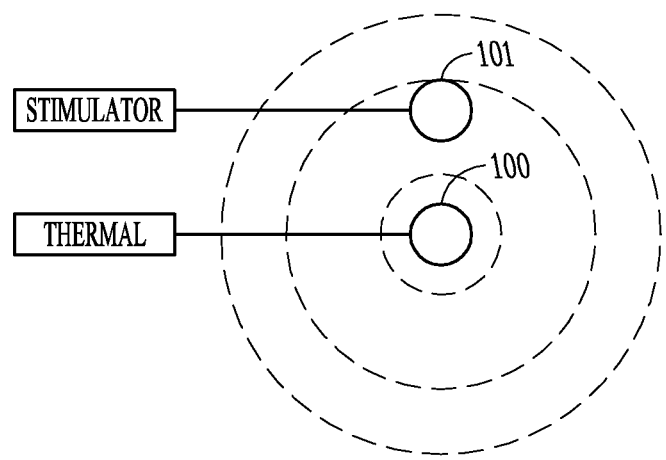
FIGS. 1A-1B illustrate an embodiment where a temperature change is used to lower a threshold of a stimulation site.

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an," "one" or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Action potentials are propagated through excitable tissue such as neural stimulation or through cardiac tissue. Temperature has an effect on the electrical characteristics of excitable tissue. Usually, increasing temperature enhances the excitability of the tissue, and lowering temperature makes it less excitable. According to various embodiments, neural or cardiac stimulation is combined with local heating or cooling to enhance or reduce the effect of the stimulation and to increase or reduce thresholds for capturing the tissue. An embodiment uses temperature modulation of the stimulation site to facilitate effective tissue excitation. Some embodiments incorporate a thermoelectric device within a lead used to pace the site, or as a separate lead placed close to the pacing site. This thermoelectric device will be used to raise or lower the temperature at the local pacing site to enhance the effect of pacing.

In a cardiac application, for example, a slight increase in temperature can be used to lower the electrical pacing threshold. An example of an application where a lower electrical pacing threshold may be beneficial is left ventricular stimulation, where phrenic stimulation may be problematic for higher pacing voltages. At least some of the energy expended to create the thermal change in the tissue may be returned back to the system in the form of energy savings due to lower pacing voltages.

Neural stimulation has been shown to be beneficial for patients with heart disease. However, neurostimulation may be accompanied by side effects. Potential side effects of vagal stimulation, for example, may include coughing, laryngeal motor fiber capture or vibration. Some side effects may be caused by excess stimulation of non-targeted tissue. In a neural application, appropriate adjustments to the temperature at the local stimulation site may allow the pacing amplitudes to be lowered, potentially reducing potential side effects. In addition, a temperature change can be used to augment a neural stimulation therapy to increase the therapeutic effect of the neural stimulation.

According to some embodiments, local temperature modulation of the target tissue close to the pacing site reduces the pacing threshold below the threshold for capturing non-targeted tissues. In addition, cool temperatures slow nerve conduction and reduce the response. Temperature can affect nerves asymmetrically.

In some embodiments, a temperature sensor is used along with a thermoelectric element. Examples of thermoelectric elements include, but are not limited to thermocouples, peltier elements, and PTC ceramic thin films. The thermal electric element can be placed close to the electrodes of the pacing lead. A temperature (above or below the body temperature) is provided local to the pacing electrode to facilitate pacing. In some embodiments, the temperature change is maintained between pacing pulses, or between episodes of pacing, such as episodes of bradycardia pacing or episodes of antitachycardia pacing (ATP). In some embodiments, the temperature change is provided in anticipation of or preparation for delivering an episode of pacing.

Some embodiments incorporate, either internally or externally, the temperature modulator independent of the stimulation system. Some embodiments use an LED light to heat tissue. LED lights are effective in heating tissue, but appear to have a relatively high energy requirement. As such, it is believed that LED lights may be particularly effective for intermittent or acute heating. Other embodiments use thermocouples. For some thermocouples, by way of examples, each 70 microvolt difference result in a 1° C. gradient. Some embodiments uses a radioisotope thermoelectric generator (RTG, RITEG), an electrical generator which obtains its power from heat released by radioactive decay. In this device, heat is converted into electricity by the Seebeck effect using an array of thermocouples. Very small amounts of a radioisotope can generate heat for a very long time.

Figure 1B:
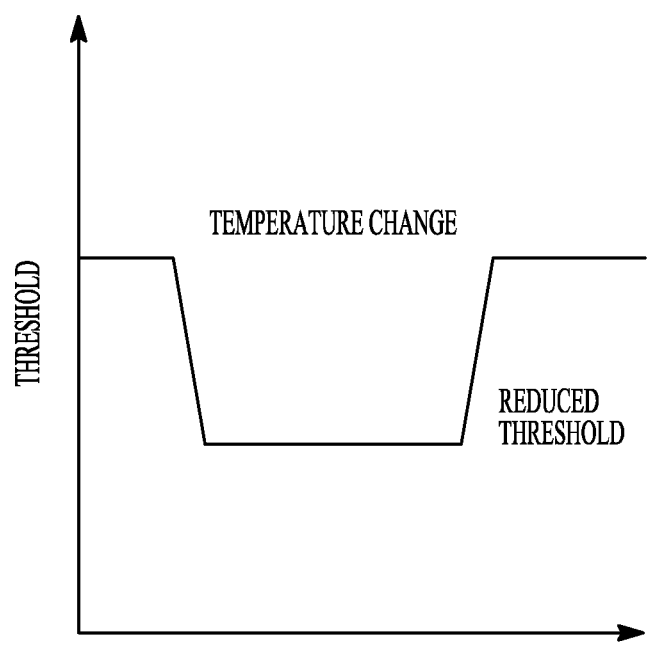

FIGS. 1A-1B illustrate an embodiment where a temperature change is used to lower a threshold of a stimulation site. FIG. 1A illustrates a thermal application site 100 and an electrical stimulation site 101, where the position of the thermal application site is proximate to the electrical stimulation site to allow temperature gradients from a temperature change of tissue at the thermal application site to change temperature of the tissue at the electrical stimulation site. The resulting temperature change at the electrical stimulation site reduces the stimulation threshold at the electrical stimulation site. FIG. 1B illustrates the reduced stimulation threshold during a time in which a thermal treatment provides a temperature change to the stimulation site.

For example, some embodiments heat a cardiac stimulation site to reduce the threshold for capturing cardiac tissue at the cardiac stimulation site. Some embodiments heat a neural stimulation site to reduce the threshold for capturing neural tissue at the neural stimulation site. Electrical stimulation of neural tissue is used as an example for stimulating neural tissue. However, the ability to reduce a stimulation threshold using a temperature change for the neural tissue would apply to other ways of stimulating nerves, such as stimulating neural activity using mechanical forces, light or ultrasound, for example. Reducing a stimulation threshold may be desirable to reduce power requirements for capturing excitable tissue, which can improve the longevity of an implanted device that is powered using a limited energy source such as a battery. Reducing a stimulation threshold may be desirable to allow a stimulation therapy to be delivered using a smaller stimulation field, where the use of the smaller stimulation field allows the therapy to avoid undesired effects of the stimulation. For example, neural stimulation in the vicinity of the heart may inadvertently stimulate the myocardium, altering intrinsic rate and activation sequence. That is, neural stimulation in the vicinity of the heart may have sufficient voltage and pulse width to capture the surrounding myocardium, resulting in unintended atrial or ventricular depolarization. In another example, stimulation of the heart can have an unintended nerve response. High output pacing can capture adjacent nerves or fat pad ganglia, which affects the neural transmitter release from these nerves. Thus, some embodiments reduce the threshold for stimulating cardiac tissue to allow a lower pacing energy to be used to reduce unintended changes in adjacent neural tissue. Other potential undesired results include inappropriate stimulation of nerves other than the target nerve, and inappropriate stimulation of smooth muscle proximate to the target nerve. The temperature change can be used to lower the stimulation threshold for the targeted nerve to allow lower energy to be used for the stimulation and avoid stimulation of the other nerves or stimulation of the smooth muscle. In another example, cardiac tissue stimulation may unintentionally stimulate a phrenic nerve.

Figure 2A:
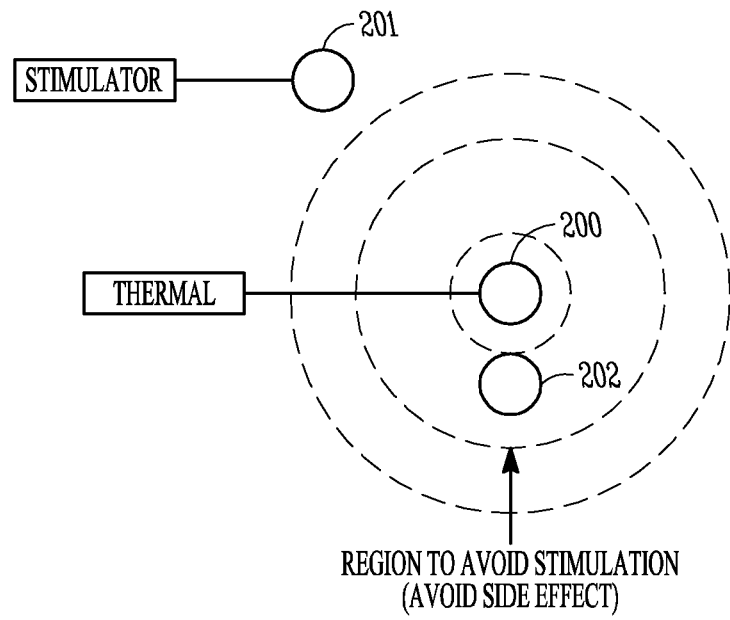
FIGS. 2A-2B illustrate an embodiment where a temperature change is used to increase a threshold of a stimulation site.
Figure 2B:
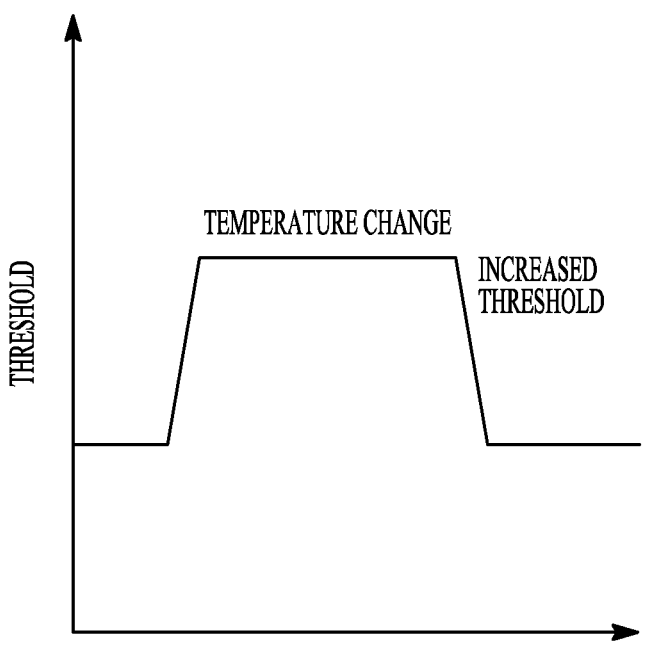

FIGS. 2A-2B illustrate an embodiment where a temperature change is used to increase a threshold of a stimulation site. FIG. 2A illustrates a thermal application site 200, an electrical stimulation site 201, and a potential side effect region 202 where it is desired to avoid stimulation that would induce an undesired action potential. The position of the thermal application site is close to the potential side effect region to allow a temperature change of tissue at the thermal application site to change temperature of the tissue at the potential side effect region. The temperature change at the potential side effect region increases the stimulation threshold at the potential side effect region. FIG. 2B illustrates the increased stimulation threshold during a time in which the temperature of tissue at the stimulation site is changed.

In an example where the potential side effect region is cardiac tissue, some embodiments cool this cardiac tissue to increase the threshold for capturing cardiac tissue at the potential side effect region. In an example where the potential side effect region is neural tissue, some embodiments cool this neural tissue to increase the threshold for capturing neural tissue at the potential side effect region. Increasing a stimulation threshold of a phrenic nerve may be desirable to avoid stimulation of a phrenic nerve during a cardiac tissue stimulation therapy. Increasing a stimulation threshold of atrial or ventricular tissue may be desired to avoid stimulation of atrial or ventricular tissue during stimulation of neural tissue near the heart such as stimulation of various vagal branches and/or neural pathways in cardiac fat pads. Also, increasing the stimulation threshold of a nerve may be desired to avoid stimulation of the nerve (e.g. laryngeal nerve) during stimulation of another nerve (e.g. vagus nerve).

Various embodiments incorporate one or more sensors for use in integrating the electrical stimulation and thermal changes. For example, some embodiments use a sensor adapted to detect a side effect. In response to a detected side effect, the stimulation threshold for the intended target is reduced using a temperature change and/or the stimulation threshold for the unintended target is increased using a temperature change. Other sensors may be used. Some embodiments use sensors and/or timers adapted to provide context for a side effect detected by a sensor or a side effect observed by the patient or clinician. By way of example, side effects may be observed only when a patient is in a particular position (e.g. standing up) or at a particular time of day. These side effects may not have been observed at the time that the stimulation device was implanted because of the patient position at the time of implantation or because of other factors that are not present in a clinical setting. Some embodiments use a posture sensor to provide context. Whenever the context is sensed or otherwise identified (e.g. any time that the patient is not lying down), the device may be programmed or otherwise configured to respond by appropriately changing a temperature of excitable tissue to avoid the anticipated side effects. Some embodiments allow the device to store posture, activity, time of day and the like whenever the side effect is detected to determine the context when the side effects are observed. According to some embodiments, the device is configured to use this contextual information to enable a side effect avoidance routine only during these contextual situations in which the side effect previously occurred.

Figure 3A:
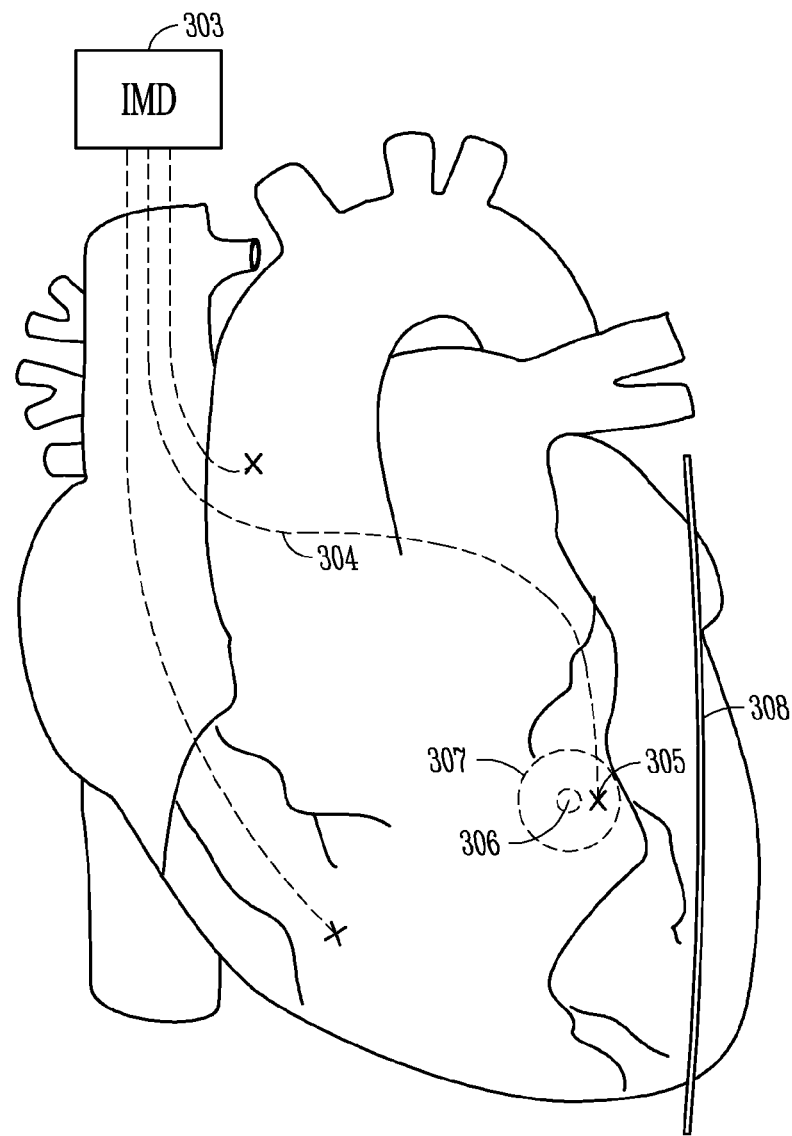
FIG. 3A illustrates a device embodiment configured to reduce the stimulation threshold of the left ventricle to avoid stimulation of the phrenic nerve.

The phrenic nerve branches into a right phrenic nerve and a left phrenic nerve, both of which pass near the heart and innervate the diaphragm below the heart. FIG. 3A illustrates a device embodiment configured to reduce the stimulation threshold of the left ventricle to avoid stimulation of the phrenic nerve. The illustrated device is an implantable medical device 303 used to perform a cardiac tissue stimulation therapy, such as CRT or various pacing therapies, using leads represented by the dotted lines and electrodes represented by "X" fed into the right atrium, right ventricle, and coronary sinus of the heart. The lead 304 passing through the coronary sinus of the heart includes a left ventricular electrode 305, or electrodes, for use to stimulate the left ventricle. A thermal electric element 306 configured to increase a temperature of the left ventricular stimulation site is also illustrated near the left ventricular electrode(s). The thermal electric element 306 may be incorporated on the same lead as the left ventricular electrode(s), or may be connected to the implantable device using another lead. In some embodiments, more than one implantable device can be used, where one device provides the cardiac tissue stimulation therapy and another device provides the desired thermal gradient 307 at the stimulation site. Thus, for example, the left ventricular pacing site can be heated to reduce the stimulation threshold for the left ventricular, which allows a smaller stimulation field to capture the left ventricle. This smaller stimulation field avoids capturing the left phrenic nerve 308 that passes near the left ventricular stimulation site.

Figure 3B:
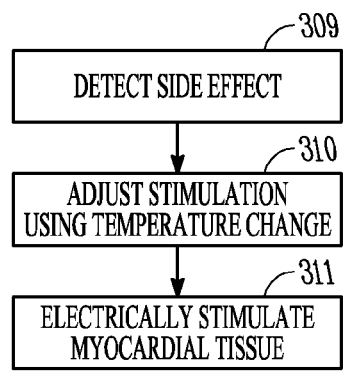
FIG. 3B illustrates an embodiment of a process to stimulate cardiac tissue and avoid phrenic nerve stimulation or avoid stimulation of other nerve tissue close to the heart.

FIG. 3B illustrates an embodiment of a process to stimulate cardiac tissue and avoid phrenic nerve stimulation or avoid stimulation of other nerve tissue close to the heart. An undesired effect of cardiac tissue stimulation may be detected, as illustrated at 309. For example, the device may detect that the pacing pulses are capturing a phrenic nerve. At 310, the effective stimulation to pace the cardiac tissue can be adjusted using a temperature change at the pacing site. The pacing site can be heated to decrease the stimulation threshold, allowing the cardiac tissue to be stimulated 311 using a reduced field that is still effective in capturing the cardiac tissue.

FIG. 4A illustrates a device embodiment 412 that provides therapeutic integration of electrical and thermal stimulation to titrate a neural stimulation therapy applied to a nerve trunk 413. The illustrated nerve trunk includes a plurality of nerve fibers. Nerve fibers can be of different sizes (e.g. A, B and C nerve fibers). The nerve fibers may conduct action potentials in different directions. For example, as represented in FIG. 4B, afferent fibers 414 conduct action potentials toward the central nervous system, and efferent fibers 415 conduct action potentials away from the central nervous system. Some fibers may be sympathetic fibers and some fibers may be parasympathetic fibers. There have been various methods proposed to selectively produce action potentials only in some of the fibers in a nerve trunk. For example, some fibers react at lower thresholds to either electrical stimulation that blocks nerve traffic or electrical stimulation that enhances nerve traffic, some proposed methods use one field to enhance nerve traffic, use another field to block or slow nerve traffic, and control the strength of these fields to selectively stimulate only some of the nerve fibers. By way of another example, some proposed methods control the direction of the current used to stimulate the nerves, thus stimulating action potentials in one direction and blocking action potentials in the other direction.

The illustrated device includes an electrical stimulation cuff 417 to electrically stimulate the nerve trunk or a portion of the fibers therein, and further includes a thermal stimulation cuff 418 to change a temperature of the nerve. FIG. 4C illustrates an example of the thermal stimulation cuff. The cuff can be designed to be a heat sink to cool the tissue within or around the cuff or a heat source to heat the tissue within or around the cuff. The cuff is designed to provide the temperature change in the interior of the cuff. Thus, the cuff substantially surrounds a volume of tissue that is to be heated or cooled, and the temperature gradient is focused toward the center of the cuff.

Multiple heat sinks and/or heat sources can surround the nerve. By way of example and not limitation, a heat sink or source can be positioned every 10 degrees around the nerve. Each heat sink or source is adjacent to a portion of the nerve trunk but not the other. The heat sink or source creates a temperature gradient across the nerve, so the nerve fibers closer to the sink or source experience the greater temperature change. A set up routine can be performed, where each heat sink or source is activated and the corresponding response is monitored until the desired response is obtained.

FIGS. 5-12 illustrate various methods, by way of example and not limitation, that can be performed using the device illustrated in FIG. 4A. As illustrated in FIG. 5, some embodiments adjust the neural stimulation threshold using a temperature change, as represented, and electrically stimulate the nerve whose threshold has been adjusted. The temperature change can be used to change a level of nerve activity before the electrical stimulation is applied to the nerve. In some embodiments the electrical stimulation is configured to diminish or block nerve traffic, and in some embodiments the electrical stimulation is configured to increase nerve traffic.

In FIG. 6, a nerve is electrically stimulated to modulate nerve activity (either increase or decrease nerve activity). The nerve activity is further adjusted or titrated using a temperature change. Thus, for example, the temperature change is used to fine tune (a slight increase or decrease to nerve traffic) the adjustment to the nerve activity caused by the electrical stimulation. The electrical stimulation can provide larger incremental changes in the therapy, and the temperature change can provide smaller incremental changes in the therapy. The different effects of temperature change and electrical stimulation on a nerve can be caused by different nerve fiber sizes, structure (e.g. myelinated or nonmyelinated) and relative position to the heat sink/source and electrode.

In FIG. 7, a temperature change is applied to a nerve to modulate nerve activity (either increase or decrease nerve activity). The nerve activity is further adjusted or titrated using electrical stimulation. Thus, for example, the electrical stimulation is used to fine tune (a slight increase or decrease to nerve traffic) the adjustment to the nerve activity caused by the temperature change. The temperature change can provide larger incremental changes in the therapy, and the electrical stimulation can provide smaller incremental changes in the therapy.

In FIG. 8, a nerve is electrically stimulated to modulate nerve activity. Nerve activity in some, but not all, nerve fibers is reduced or blocked using temperature change. The net result of the electrical stimulation and thermal stimulation is to increase nerve activity in only some of the fibers in the nerve trunk. For example, the temperature change reduces the intensity of the therapy that would otherwise be delivered by the electrical stimulation. For example, if afferent fibers are electrically stimulated, nerve activity in some afferent fibers may be blocked or reduced using a temperature change.

In FIG. 9, a temperature changed is applied to a nerve to modulate nerve activity. Nerve activity in some, but not all, nerve fibers is reduced or blocked using electrical stimulation. The net result of the electrical stimulation and thermal stimulation is to increase nerve activity in only some of the fibers in the nerve trunk.

In FIG. 10, electrical stimulation is chronically applied to a nerve. A temperature change is used to provide an acute or an intermittent modulation of the nerve traffic. Thus, for example, the electrical stimulation can be delivered as part of a therapy for a chronic disease, and the thermal stimulation can be delivered in response to episodes indicated for treatment using neural stimulation.

In FIG. 11, a thermal change is chronically applied to a nerve to modulate nerve activity. Electrical stimulation is used to provide an acute or intermittent modulation for the nerve activity. In an embodiment in which therapy is timed to respiration, a chronic thermal change is applied. Neural stimulation is acutely delivered, timed to respiration, to reduce sympathetic activity during inspiration. In another embodiment, acute neural stimulation is applied to compensate for possible intermittent side effects caused by the temperature change. For example, stimulation of vagal activity in the cervical region can cause a cough sensation. Acute stimulation can be used to reduce or eliminate the cough sensation. In another example, sympathetic activity is reduced or blocked with chronically applied cooling. If decompensation, arrhythmia, or arrhythmia triggers are detected, artificial electrical stimulation provides some sympathetic activity to the heart.

In FIG. 12, a nerve activity in a first direction (either afferent or efferent directions) is modulated using electrical stimulation to provide either an increase or a decrease in nerve traffic in the first direction. Nerve activity in a second direction (the other of the afferent or efferent directions) is modulated using thermal stimulation to provide either an increase or decrease in nerve traffic in the second direction. By way of example and not limitation, an embodiment captures afferent vagal fibers for a chronic therapy using electrical stimulation, and a heat sink is positioned on the vagus nerve between the electrically-stimulated region of the vagus nerve and the heart to reduce efferent action potentials toward the heart.

Figure 13:
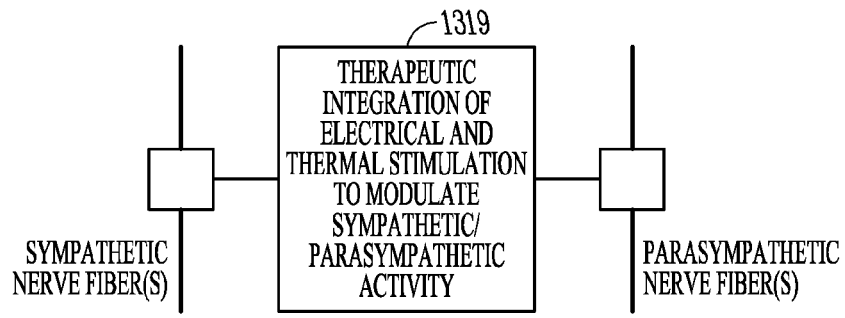
FIG. 13 illustrates a device embodiment to therapeutically integrate electrical and thermal stimulation to modulate sympathetic and parasympathetic activity.

A device embodiment 1319 to therapeutically integrate electrical and thermal stimulation to modulate sympathetic and parasympathetic activity is generally illustrated in FIG. 13. The figure illustrates sympathetic nerve fiber(s) and parasympathetic nerve fiber(s). These sympathetic and parasympathetic nerve fibers may be in the same nerve trunk, as in the vagus nerve, may be in distinct nerve trunks or may include neural targets (e.g. targets associated with baroreceptors or chemoreceptors) in distinct locations. These neural targets may be stimulated with devices similar to nerve cuffs or using transvascular stimulation. According to some embodiments, one of the sympathetic and parasympathetic targets is electrically stimulated and the other is thermally stimulated or treated.

Figure 14:
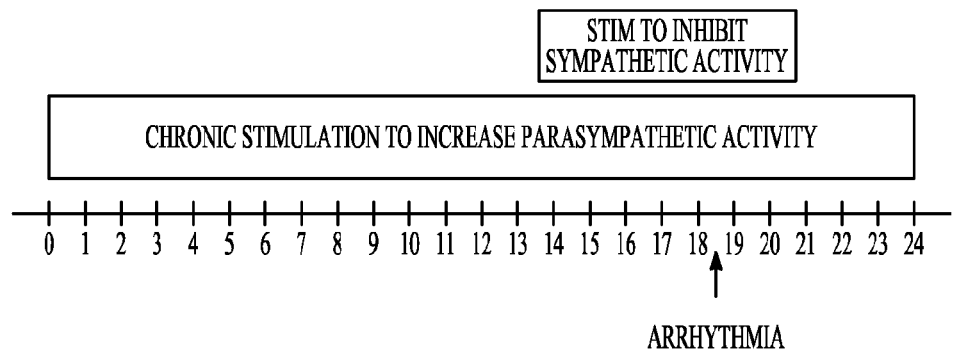
FIG. 14 illustrates an example of modulating sympathetic and parasympathetic activity as part of an integrated therapy, according to various embodiments.

FIG. 14 illustrates an example of modulating sympathetic and parasympathetic activity as part of an integrated therapy, according to various embodiments. A chronic neural stimulation therapy is applied to increase parasympathetic activity throughout a day. In response to an event, an acute stimulation therapy is delivered to inhibit sympathetic activity. For example, a programmable neural stimulator can be programmed to implement an anti-arrhythmia therapy by decreasing sympathetic activity in the sympathetic nerves if the arrhythmia detector detects the cardiac arrhythmia, and implement a chronic heart failure therapy by chronically increasing parasympathetic activity in the parasympathetic nerves. This embodiment can be combined with various cardiac rhythm management devices (e.g. implantable cardioverter/defibrillator) that detect and treat arrhythmias. According to some embodiments, one of the chronic or acute stimulation is electrical and the other is thermal.

In an embodiment, the system includes a respiratory sensor, and the programmable neural stimulator is programmed to time delivery of electrical stimulation and temperature modulation to decrease sympathetic activity during the inspiratory phase, and to increase parasympathetic activity during the expiratory phase. In some embodiments, the respiration sensor can be used to guide the neural stimulation to block or reduce sympathetic activity during the inspiratory phase when sympathetic activity is intrinsically high, and to stimulate the vagus nerve during an expiratory phase to enhance the parasympathetic activity.

Figure 15:
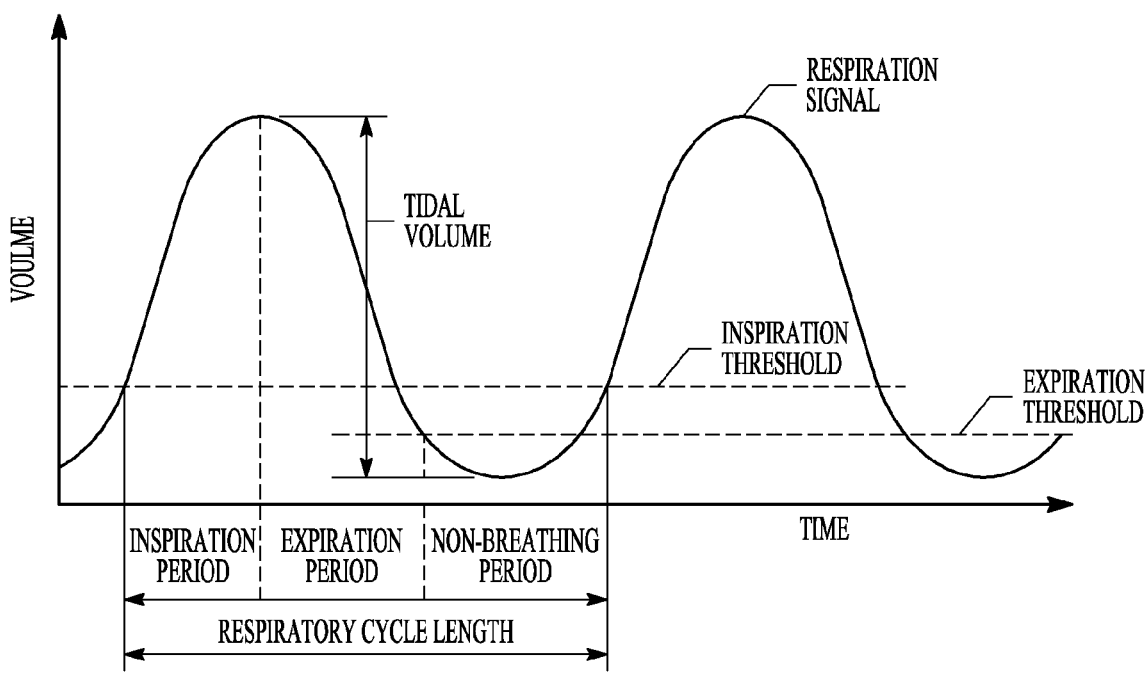
FIG. 15 is an illustration of a respiratory signal indicative of respiratory cycles and respiratory parameters including respiratory cycle length, inspiration period, expiration period, non-breathing period, and tidal volume.

FIG. 15 is an illustration of a respiratory signal indicative of respiratory cycles and respiratory parameters including respiratory cycle length, inspiration period, expiration period, non-breathing period, and tidal volume. The inspiration period starts at the onset of the inspiration phase of a respiratory cycle, when the amplitude of the respiratory signal rises above an inspiration threshold, and ends at the onset of the expiration phase of the respiratory cycle, when the amplitude of the respiratory cycle peaks. The expiration period starts at the onset of the expiration phase and ends when the amplitude of the respiratory signal falls below an expiration threshold. The non-breathing period is the time interval between the end of the expiration phase and the beginning of the next inspiration phase. The tidal volume is the peak-to-peak amplitude of the respiratory signal.

Figure 16:
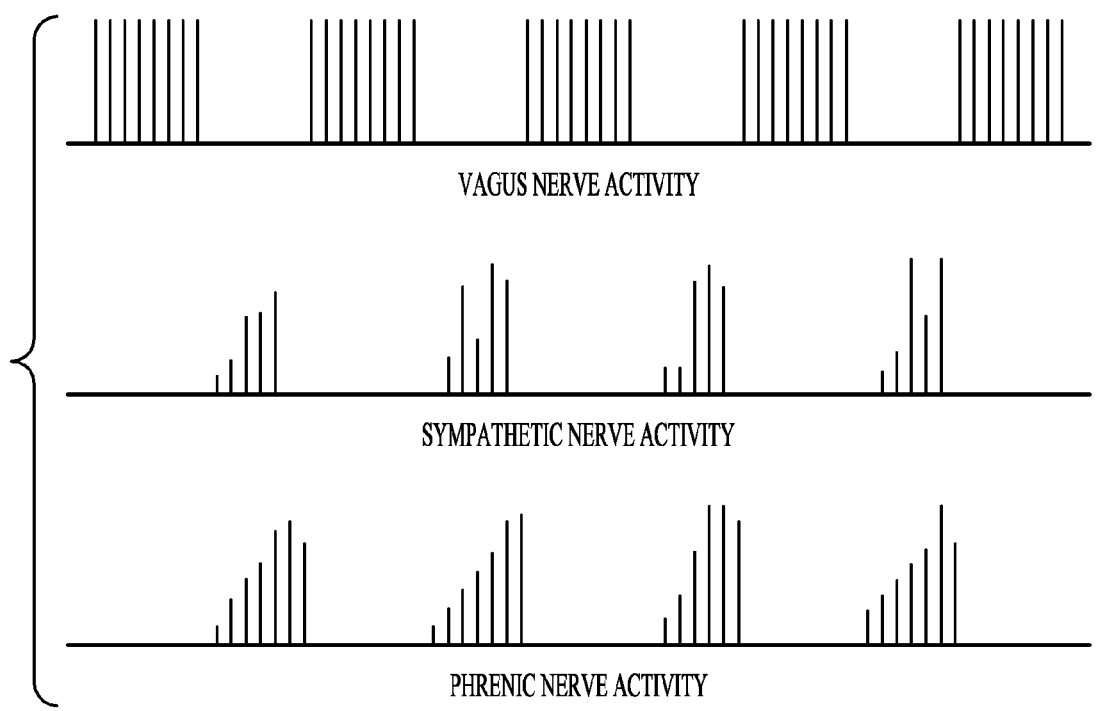
FIG. 16 illustrates the relationship between respiration, as illustrated by phrenic nerve activity, and both sympathetic nerve activity and vagus nerve activity.

FIG. 16 illustrates the relationship between respiration, as illustrated by phrenic nerve activity, and both sympathetic nerve activity and vagus nerve activity. As illustrated, sympathetic nerve activity is most active during periods where the phrenic nerve activity is active, and parasympathetic nerve activity is most active during periods when the phrenic nerve activity is inactive.

According to some embodiments, timing is provided to decrease sympathetic activity during the inspiratory phase and to increase parasympathetic activity during the expiratory phase. For some embodiments, timing is provided to decrease sympathetic activity during the inspiratory phase, and increase parasympathetic activity during the inspiratory phase. For some embodiments, sympathetic activity is chronically decreased, and timing is provided, with respect to either the expiration phase or the inspiration phase of the respiratory cycle, to intermittently increase parasympathetic activity. In some embodiments, parasympathetic activity is chronically increased, and timing is provided, with respect to either the inspiration phase of the respiratory cycle, to intermittently decrease sympathetic activity.

The respiratory signal is a physiologic signal indicative of respiratory activities. In various embodiments, the respiratory signal includes any physiology signal that is modulated by respiration. In one embodiment, the respiratory signal is a transthoracic impedance signal sensed by an implantable impedance sensor. In another embodiment, the respiratory signal is extracted from a blood pressure signal that is sensed by an implantable pressure sensor and includes a respiratory component. In another embodiment, the respiratory signal is sensed by an external sensor that senses a signal indicative of chest movement or lung volume. According to various embodiments, peaks of a respiratory signal are detected as respiratory fiducial points. At least one delay interval starts upon the detection of each of peaks. Therapy (e.g. burst of neural stimulation pulses and temperature) is delivered to a nerve such as the vagus nerve when delay interval expires. In various other embodiments, onset points of the inspiration phases, ending points of the expiration phases, or other threshold-crossing points are detected as the respiratory fiducial points.

Figure 17:
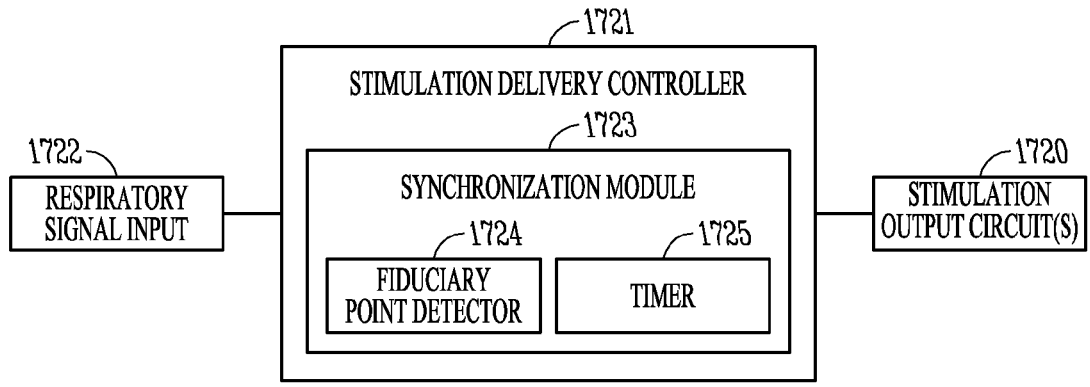
FIG. 17 illustrates a respiration-controlled neural stimulation circuit, including a stimulation output circuit 1720, a controller 1721 and a respiratory signal input 1722.

FIG. 17 illustrates a respiration-controlled neural stimulation circuit, including a stimulation output circuit 1720, a controller 1721 and a respiratory signal input 1722. The illustrated controller 1721 includes a synchronization module 1723 with a fiduciary point detector 1724 and a timer 1725. The respiratory signal input receives the respiratory signal indicative of respiratory cycles and respiratory parameters, and the synchronization module synchronizes the delivery of the neural stimulation and temperature modulation to the respiratory cycles. The respiratory fiducial point detector detects predetermined-type respiratory fiducial points in the respiratory signal, and a delay timer times the delay interval starting with each of the detected respiratory fiducial points. The stimulation delivery controller causes the stimulation output circuit to deliver stimulation when the delay interval expires.

Figure 18A:
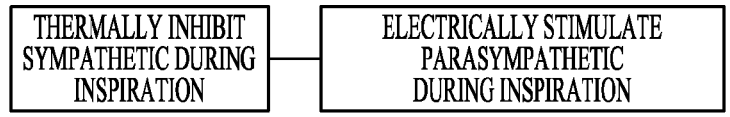
FIGS. 18-21 illustrate various therapy embodiments in which stimulation is timed to respiration.
Figure 18B:
Figure 19:
Figure 20A:
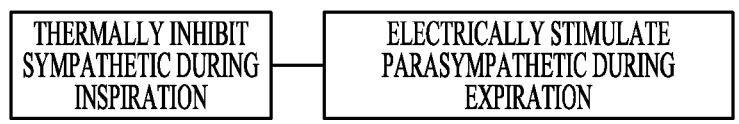
Figure 20B:
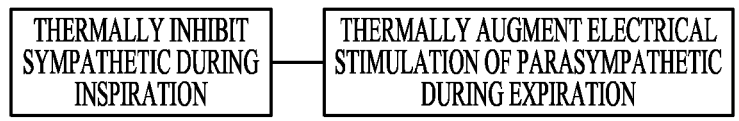
Figure 21:
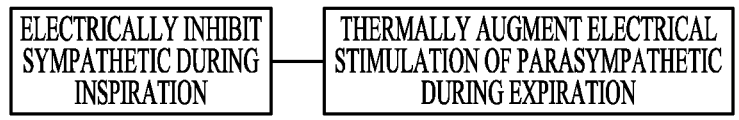

The thermal or electrical stimulation can be applied to neural targets (e.g. parasympathetic or sympathetic) to provide a desired effect (e.g. stimulate/augment or inhibit) for neural activity during different stimulation times of the respiratory cycle (e.g. inspiration phase or portion thereof, or expiration phase or portion thereof). Any combination of these targets, effects, and stimulation times can be used. The particular combinations can be chosen to provide a desired therapeutic benefit. For example, FIGS. 18A-18B, FIG. 19, FIGS. 20A-20B and FIG. 21 illustrate embodiments, by way of example and not limitation, to provide a desired therapeutic benefit for use in a heart failure therapy. FIGS. 18A-18B and 19 relate to sympathetic activity during inspiration. FIGS. 18A-18B are further related to thermally inhibiting sympathetic activity during inspiration. In FIG. 18A, parasympathetic activity is electrically stimulated during inspiration. In FIG. 18B, parasympathetic activity is electrically stimulated during inspiration, and this electrical stimulation is thermally augmented during inspiration. In the example identified in FIG. 19, sympathetic activity is electrically inhibited during inspiration. Parasympathetic activity is electrically stimulated during inspiration, and this electrical stimulation is thermally augmented during inspiration. FIGS. 20A-20B and 21 relate to parasympathetic activity during expiration. FIGS. 20A-20B are further related to thermally inhibiting sympathetic activity during inspiration. In FIG. 20A, parasympathetic activity is electrically stimulated during expiration. In FIG. 20B, parasympathetic stimulation is electrically stimulated during expiration, and this stimulation is thermally augmented during expiration. In the example identified in FIG. 21, sympathetic activity is electrically inhibited during inspiration. Parasympathetic activity is electrically stimulated during expiration and this electrical stimulation is thermally augmented during expiration.

Various neural stimulation therapies can be integrated with various cardiac tissue stimulation therapies. The integration of therapies may have a synergistic effect. Therapies can be synchronized with each other, and sensed data can be shared. A cardiac tissue stimulation therapy provides a cardiac therapy using electrical stimulation of the myocardium or other cardiac tissue. Some examples are provided below.

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Figure 22:
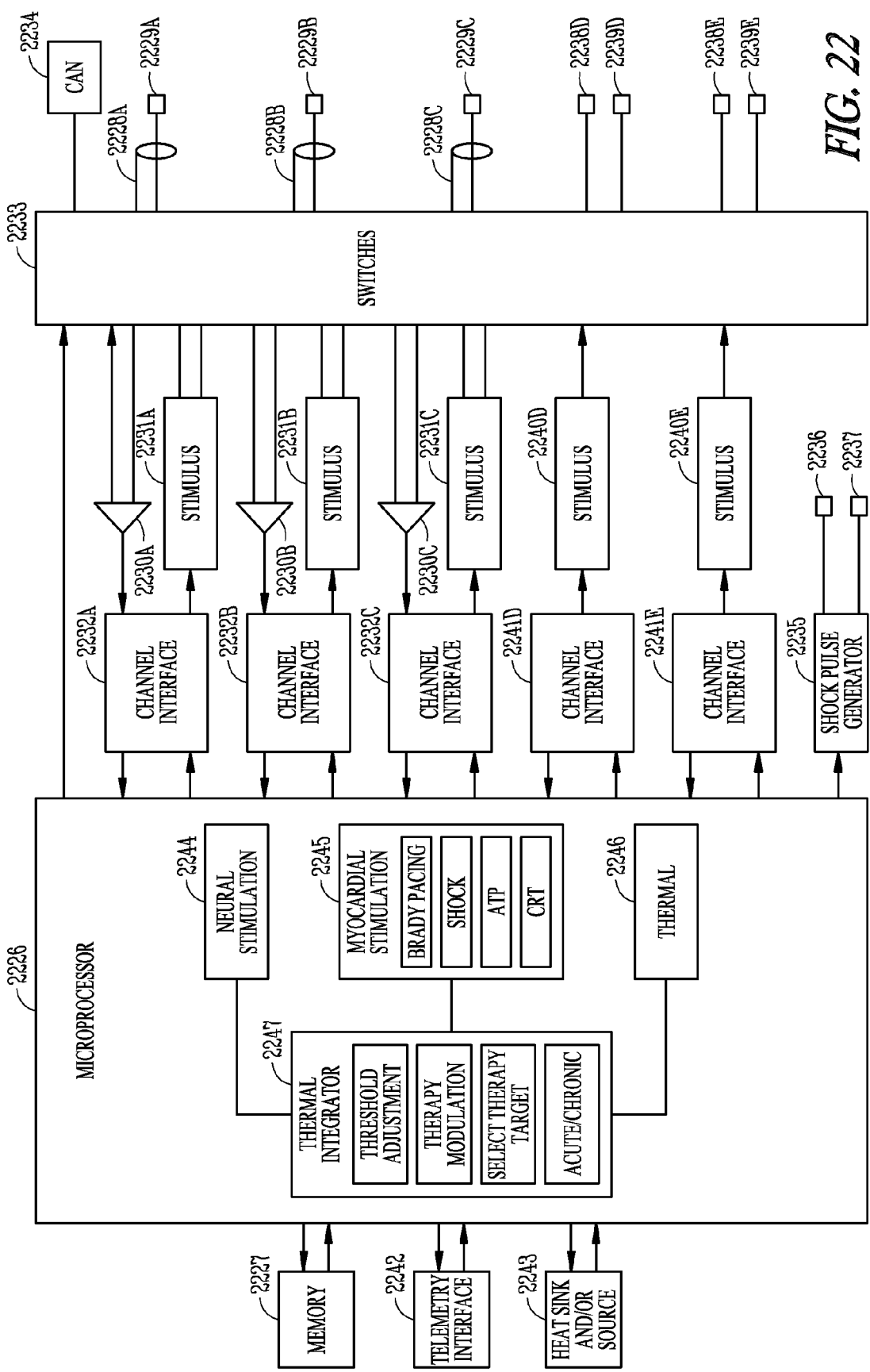
FIG. 22 shows a system diagram of an embodiment of a microprocessor-based implantable device, according to various embodiments.

FIG. 22 shows a system diagram of an embodiment of a microprocessor-based implantable device, according to various embodiments. The controller of the device is a microprocessor 2226 which communicates with a memory 2227 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 2228A-C and tip electrodes 2229A-C, sensing amplifiers 2230A-C, pulse generators 2231A-C, and channel interfaces 2232A-C. Each channel thus includes a pacing channel made up of the pulse generator connected to the electrode and a sensing channel made up of the sense amplifier connected to the electrode. The channel interfaces communicate bidirectionally with the microprocessor, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 2233 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 2234 or an electrode on another lead serving as a ground electrode. A shock pulse generator 2235 is also interfaced to the controller for delivering a defibrillation shock via a pair of shock electrodes 2236 and 2237 to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 2238D and a second electrode 2239D, a pulse generator 2240D, and a channel interface 2241D, and the other channel includes a bipolar lead with a first electrode 2238E and a second electrode 2239E, a pulse generator 2240E, and a channel interface 2241E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links. The figure illustrates a telemetry interface 2242 connected to the microprocessor, which can be used to communicate with an external device. The illustrated device further includes a heat source and/or sink 2243 (e.g. a thermoelectric device) for use in providing local temperature changes for thermal applications.

The illustrated microprocessor 2226 is capable of performing neural stimulation therapy routines 2244, cardiac tissue (e.g. myocardial) stimulation routines 2245, and thermal routines 2246. Examples of NS therapy routines include a heart failure therapy, an anti-hypertension therapy (AHT), anti-remodeling therapy (ART), and anti-arrhythmia therapy. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT). Examples of thermal stimulation routines include locally heating or cooling targeted tissue. The illustrated controller is able to perform routines 2247 to integrate thermal stimulation with neural stimulation and/or myocardial stimulation to lower stimulation thresholds, to enhance therapy, to selectively stimulate neural targets, or to perform acute and chronic therapies using thermal stimulation and neural stimulation. Various examples of integrating thermal stimulation and electrical stimulation are provided previously. Additional sensors, such as respiration sensors, may be incorporated in the illustrated system. The neural stimulation and cardiac rhythm management functions may be integrated in the same device, as generally illustrated in FIG. 22 or may be separated into functions performed by separate devices.

One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An implantable system for delivering therapy, comprising:
    at least one of a heat sink configured to reduce temperature of excitable tissue or a heat source configured to increase temperature of excitable tissue;
    a pulse generator and at least one stimulation electrode configured to deliver electrical stimulation to excitable tissue;
    a memory with instructions for performing at least one stimulation routine to electrically stimulate the excitable tissue and for performing at least one thermal routine to change the temperature of the excitable tissue, and further with integration instructions for performing an integration routine to integrate the at least one thermal routine with the at least one stimulation routine; and
    a controller configured to operate on the instructions to perform the at least one stimulation routine to electrically stimulate the excitable tissue using the pulse generator and the at least one stimulation electrode, to perform the at least one thermal routine to change temperature of the excitable tissue using the heat sink or the heat source, and to operate on the integration instructions to perform the integration routine to integrate the at least one thermal routine with the at least one stimulation routine,
    wherein in performing the integration routine the controller is configured to coordinate timing between changing temperature of the excitable tissue and electrically stimulating the excitable tissue, wherein the system is implantable in a patient having a chronic condition indicated for a chronic therapy and further having an acute condition indicated for an acute therapy, and the controller is configured to:

apply electrical stimulation for the chronic therapy and change temperature for the acute therapy: or apply electrical stimulation for the acute therapy and change temperature for the chronic therapy; or apply electrical stimulation for the chronic therapy and change temperature for the acute therapy, and apply electrical stimulation for the acute therapy and change temperature for the chronic therapy.

2. The system of claim 1, wherein the pulse generator and the at least one stimulation electrode are configured to deliver electrical stimulation to nerve tissue.

3. The system of claim 2, wherein the integration instructions to be operated on by the controller include instructions for adjusting temperature to modulate nerve activity in the electrically stimulated nerve tissue.

4. The system of claim 2, wherein the integration instructions to be operated on by the controller include instructions for adjusting temperature to selectively encourage or inhibit nerve activity in the electrically stimulated nerve tissue.

5. The system of claim 1, wherein the pulse generator and the at least one stimulation electrode are configured to deliver electrical stimulation to cardiac tissue.

6. The system of claim 1, wherein the integration instructions to be operated on by the controller include instructions for adjusting temperature to adjust a stimulation threshold for electrically stimulating and capturing the excitable tissue.

7. The system of claim 1, wherein the system is configured to implement a method for stimulating cardiac tissue, comprising:

changing a stimulation threshold of excitable tissue from a first level to a second level in preparation for stimulating the nerve tissue, wherein changing the stimulation threshold of the excitable tissue includes changing a temperature of the excitable tissue; and stimulating the nerve tissue at a stimulation site when the stimulation threshold is at the second level.

8. The system of claim 7, wherein changing the stimulation threshold of excitable tissue includes changing the stimulation threshold of the cardiac tissue.

9. The system of claim 8, wherein changing the stimulation threshold of the cardiac tissue includes reducing the stimulation threshold of the cardiac tissue from the first level to the second level.

10. The system of claim 9, wherein reducing the stimulation threshold of the cardiac tissue includes increasing the temperature of the cardiac tissue.

11. The system of claim 7, wherein changing the stimulation threshold of excitable tissue includes changing the stimulation threshold of nerve tissue.

12. The system of claim 11, wherein changing the stimulation threshold of nerve tissue includes increasing the stimulation threshold of the nerve tissue from the first level to the second level.

13. The system of claim 12, wherein increasing the stimulation threshold of the nerve tissue includes decreasing the temperature of the nerve tissue.

14. The system of claim 11, wherein changing the stimulation threshold of nerve tissue includes increasing the stimulation threshold of a phrenic nerve.

15. The system of claim 1, wherein the system is configured to implement a method for stimulating nerve tissue, comprising:

the controller is configured to operate on the integration instructions to change the temperature of the excitable tissue to change the response of the excitable tissue to the electrical stimulation.

16. The system of claim 15, wherein changing the stimulation threshold of excitable tissue includes changing the stimulation threshold of the nerve tissue at the stimulation site.

17. The system of claim 16, wherein changing the stimulation threshold of the nerve tissue at the stimulation site includes decreasing the stimulation threshold of the nerve tissue at the stimulation site, wherein decreasing the stimulation threshold includes increasing temperature of the nerve tissue at the stimulation site.

18. The system of claim 15, wherein changing the stimulation threshold of excitable tissue includes changing the stimulation threshold of other nerve tissue at another site than the stimulation site.

19. The system of claim 18, wherein changing the stimulation threshold of other nerve tissue includes increasing the stimulation threshold of the other nerve tissue, wherein increasing the stimulation threshold includes decreasing temperature of the nerve tissue at the stimulation site.

20. The system of claim 1, wherein:

the integration instructions in the memory include integration instructions for modifying a response of the excitable tissue to the electrical stimulation by changing temperature of the excitable tissue; and changing a stimulation threshold of excitable tissue from a first level to a second level in preparation for stimulating the cardiac tissue, wherein changing the stimulation threshold of the excitable tissue includes changing a temperature of the excitable tissue; and stimulating the cardiac tissue when the stimulation threshold is at the second level.

21. The system of claim 1, wherein:

the integration instructions in the memory include integration instructions to electrically stimulate a nerve to modulate nerve activity and to change temperature in the nerve to block or reduce nerve traffic in some fibers of the nerve; and the controller is configured to operate on the integration instructions to electrically stimulate the nerve to modulate nerve activity and to change temperature in the nerve to block or reduce nerve traffic in some fibers of the nerve.

22. The system of claim 1, wherein:

the integration instructions in the memory include integration instructions to change temperature to modulate nerve activity in a nerve and to electrically stimulate the nerve to block or reduce nerve traffic in some fibers of the nerve; and the controller is configured to operate on the integration to change temperature to modulate nerve activity in a nerve and to electrically stimulate the nerve to block or reduce nerve traffic in some fibers of the nerve.

23. The system of claim 1, further comprising a respiration detector configured to detect respiration and inspiration, wherein the integration instructions in the memory include integration instructions to change temperature to inhibit sympathetic nerve activity during inspiration, and to electrically stimulate parasympathetic nerve activity during inspiration.

24. The system of claim 1, further comprising a respiration detector configured to detect respiration and inspiration, wherein the integration instructions in the memory include integration instructions to electrically inhibit sympathetic nerve activity during inspiration and to thermally augment parasympathetic nerve activity during inspiration.

* * * * *